US009101499B2

(12) United States Patent
Haggas (10) Patent No.: US 9,101,499 B2
(45) Date of Patent: Aug. 11, 2015

(54) PROSTHETIC APPARATUS AND ARTIFICIAL JOINT

(75) Inventor: John Stephen Haggas, West Yorkshire (GB)

(73) Assignee: HUGH STEEPER LIMITED, Leeds (GB)

( * ) Notice: Subject to any disclaimer, the term of this patent is extended or adjusted under 35 U.S.C. 154(b) by 418 days.

(21) Appl. No.: 13/381,744

(22) PCT Filed: Jun. 28, 2010

(86) PCT No.: PCT/GB2010/001247
§ 371 (c)(1),
(2), (4) Date: Aug. 16, 2012

(87) PCT Pub. No.: WO2011/001136
PCT Pub. Date: Jan. 6, 2011

(65) Prior Publication Data
US 2013/0053984 A1    Feb. 28, 2013

(30) Foreign Application Priority Data

Jul. 2, 2009   (GB) .................................. 0911510.6
Jul. 2, 2009   (GB) .................................. 0911511.4
Jan. 28, 2010  (GB) .................................. 1001443.9
Apr. 30, 2010  (GB) .................................. 1007272.6

(51) Int. Cl.
 A61F 2/58    (2006.01)
 A61F 2/68    (2006.01)
 B25J 15/00   (2006.01)
 B25J 15/10   (2006.01)
 A61F 2/70    (2006.01)
 A61F 2/50    (2006.01)
 A61F 2/76    (2006.01)

(52) U.S. Cl.
CPC ............... *A61F 2/583* (2013.01); *A61F 2/586* (2013.01); *A61F 2/68* (2013.01); *A61F 2/585* (2013.01); *A61F 2/70* (2013.01); *A61F 2002/5001* (2013.01); *A61F 2002/5093* (2013.01); *A61F 2002/701* (2013.01); *A61F 2002/704* (2013.01); *A61F 2002/762* (2013.01); *A61F 2002/7625* (2013.01); *B25J 15/0009* (2013.01); *B25J 15/10* (2013.01)

(58) Field of Classification Search
None
See application file for complete search history.

(56) References Cited

U.S. PATENT DOCUMENTS

| 6,896,704 B1 * | 5/2005 | Higuchi et al. ................. 623/64 |
| 2008/0200994 A1 | 8/2008 | Colgate et al. |
| 2009/0326677 A1 | 12/2009 | Phillips et al. |

FOREIGN PATENT DOCUMENTS

| GB | 2 146 406 | 4/1985 |
| GB | 2 278 281 | 11/1994 |
| WO | 03/017881 | 3/2003 |

OTHER PUBLICATIONS

Ito K. et al., "Compliance control . . . ultrasonic motors", Intelligent Robots and Systems, 1994, "advanced Robotic Systems and the Real World", IROS, Sep. 1994, New York, NY USA, vol. 3, pp. 1816-1823 XP010142057.

*Primary Examiner* — David H Willse
(74) *Attorney, Agent, or Firm* — Clark & Brody (57) ABSTRACT

An artificial joint with two degrees of freedom has two rotary motors that move the joint in one degree of freedom when operated in respective senses of rotation and move the joint in the other degree of freedom when one of the motors is reversed. The movement depends on balancing the operation of the motors, which are controlled by a microprocessor. Sensors on the joint are connected to the microprocessor in a closed-loop feedback. A prosthetic device includes a tendon received in one end of a slot in a movable member, whereby movement of the tendon moves the movable member. A prosthesis has two parts moveable relative to one another, an actuator, and a user control. A transducer connected to the control and the actuator provides signals indicating movement effected by the actuator. A prosthesis cover includes a silicone laminate and a reinforcing liner.

5 Claims, 10 Drawing Sheets

Fig.13
Basic grip maintenance

Fig.16 Precision

Fig.15 Key

Fig.14 Point

PROSTHETIC APPARATUS AND ARTIFICIAL JOINT

A first aspect of the present invention relates to an artificial joint.

One such joint that has been proposed hitherto comprises a prosthetic wrist in which respective motors control flexing of the wrist and relative rotation of the wrist parts of the joint.

A disadvantage of such a prior construction is the extent to which the operation of the respective motors can be combined.

The first aspect of the present invention seeks to provide a remedy.

Accordingly, the first aspect of the present invention is directed to an artificial joint having at least two degrees of freedom of movement and at least two rotary motors arranged to effect movement of the joint in one of those degrees of freedom when the motors operate in respective given senses of rotation and to effect movement of the joint in the other of those at least two degrees of freedom when the sense of rotation of one of the motors is reversed, so that the actual movement of the joint is dependent upon a balancing of the operation of the said at least two rotary motors, in which those motors are connected to a microprocessor for control thereby, and sensors are provided on the joint to monitor the operation of those motors, the sensors also being connected to the microprocessor to effect a closed loop feedback control in the operation of the motors.

Preferably, the artificial joint comprises a prosthetic wrist.

One of the said at least two degrees of freedom of movement may comprise a flexing of the joint.

The other of the said at least two degrees of freedom of movement may comprise a relative rotation between two parts of the joint.

At least one of the sensors may comprise a device constructed and arranged to monitor the angular position of the rotor of one of the motors.

Alternatively, or in addition, at least one of the sensors may comprise a device which is constructed and arranged to observe movement of one part of the joint relative to another.

One or more of the sensors may comprise a linear encoder, a potentiometer or a Hall effect sensor, for example.

The first aspect of the present invention extends to a prosthesis comprising a prosthetic hand portion and a lower arm portion interconnected by a prosthetic wrist in accordance with the invention.

The second aspect of the present invention relates to a cover for a prosthesis.

Hitherto, covers for prostheses, such as a prosthetic hand have comprised either a relatively strong plastics material which, though hardwearing, is not very lifelike, or have comprised a more lifelike material which is not hardwearing.

The second aspect of the present invention seeks to provide a remedy.

Accordingly, the second aspect of the present invention is directed to a cover for a prosthesis comprising a silicone rubber laminate and a reinforcing liner on the intended underside of the laminate bonded thereto.

Preferably, the silicone rubber laminate comprises from 9 to 12 layers.

Advantageously, one or more outer layers of the laminate comprise a material which gives a good wear resistance and a relatively high tear strength whilst at the same time providing good, elasticity.

Each layer of the laminate may be substantially 0.12 mm thick.

One or more layers of the laminate within the outermost layer or layers may comprise a material which gives the cover a softness and high degree of flexibility and also renders the cover lifelike and close in appearance and behaviour to human skin.

Preferably, the reinforcing liner comprises nylon, more preferably woven nylon stocking material.

The bonding between the laminate and the liner may be by means of further silicone material which encapsulates the liner and which is bonded to the laminate. As a result, the portions of the mechanical prosthesis can glide over the inside of the cover to give a relatively low frictional engagement between the cover and the mechanical parts.

The cover is especially useful if it is in the shape of a hand.

Prosthetic nails, for example fingernails, may be formed on the cover. The nails may comprise layers of silicone.

For a lifelike appearance, at least one of the layers of silicone of each nail is coloured pink and at least one of the layers outside the pink layer is clear. The layers of silicone which constitute each nail may collectively be substantially 2 to 3 mm thick.

The second aspect of the present invention extends to a method of making a cover for a prosthesis. More especially, such a method may comprise building up successive layers of liquid silicone rubber on the inside of a mould, preferably a mould having a glove-shaped interior, which has been warmed and pretreated with release agent. The laminate cover pre-form may now be removed from the mould, turned inside out, and placed on to a mandrel. A reinforcing layer, such as woven nylon, may now be placed on to the laminate, whereafter one or more further coatings of liquid silicone rubber may be applied to the woven nylon. The strand diameter of the woven nylon may be in the range from 0.1 to 0.5 mm. The mandrel with the finished cover may be placed into a hot oven to cure the material of the cover. After heating, the mandrel with cover is removed from the oven and allowed to cool, whereafter the cover may be peeled off from the mandrel.

The third aspect of the present invention relates to a prosthetic device comprising a tendon having a portion which engages a movable member of the device, so that movement of the tendon in a given direction urges the said movable member correspondingly.

A number of such constructions in prosthetic devices which have been proposed hitherto have involved complex and expensive linkages to effect a more lifelike movement of the movable member. However, such constructions have also been susceptible to damage if the prosthetic device is accidentally knocked or forced against an external object.

The third aspect of the present invention seeks to provide a remedy.

Accordingly, the third aspect of the present invention is directed to a prosthetic device having the construction set out in the opening paragraph of the present specification, in which the said portion engages the said movable member by being received in one end of a slot within the movable member, the slot extending from the said end in a direction opposite to the said given direction.

Preferably, the tendon has a further portion spaced from the first-mentioned portion, which further portion is connected to drive means of the device, which drive means may comprise a linear actuator.

—A—

The device may be further provided with resilient means to act on the movable member against the action of the tendon when the latter moves in the said given direction.

This provides the advantage that the force of the drive means only needs to be effective in one direction since release of that force enables the resilient means to move the movable member in the opposite sense or direction from that caused by the drive means.

The resilient means may comprise a resilient cover of the prosthetic device.

In one embodiment of the invention, the movable member comprises a phalange.

More especially, the phalange may comprise or be part of a finger connected to a palm of the prosthetic device. In that case the drive means may be secured within the palm of the prosthetic device. Movement of the tendon in the said given direction may effect closure of the finger.

The fourth aspect of the present invention relates to a prosthesis comprising at least two parts which are moveable relative to one another, an actuator connected to move one of the parts relative to the other, and a control connected to operate the actuator in dependence upon a signal issued to the control by the user.

A hand prosthesis having this construction which has already been proposed comprises two parts mechanically linked to move together between a fully open position and a fully closed position, the fully opened position being a known constant. This enables the user to know how to position the hand to ensure that the fully closed position will effect the desired grip.

Increasingly prostheses offering more than one kind of movement are being made available, so that for example one hand prosthesis already proposed can be commanded by the user to selectively effect a first movement following which the hand prosthesis adopts a pointing configuration, or a second movement to effect a pincer grip. Such a prosthesis is so constructed that it positions the moveable parts in a known position, such as a fully open position, before applying appropriate power of movement to the moveable parts to effect the first or the second movement. It needs to start from such a reference configuration to ensure that the end position after the movement is correct. This is important in enabling the user to position the hand prosthesis as a whole to make the movement effective.

A problem encountered with such a prosthesis is that useful energy may be wasted whilst it is first moved into the reference configuration. Furthermore changes in frictional forces between moving parts over time may alter the resulting positions of the parts after a given signal has been issued to the control by the user.

The fourth aspect of the present invention seeks to provide a remedy to one or more of these problems.

Accordingly, the present fourth aspect of the invention is directed to a prosthesis having the construction set out in the opening paragraph of the present specification, in which a movement transducer is connected to the control, and also to the actuator to provide signals to the control indicative of the amount of movement effected by the actuator, and the control operates the actuator in dependence upon the signals it receives from the transducer.

The prosthesis may comprise a hand prosthesis.

The movement transducer may comprise a digital pulse encoder.

The control may be programmed to change the power applied to the actuator in dependence upon the difference between the actual relative position between the relatively moveable parts and a desired relative position stored in the control.

The actuator may comprise an electrical motor.

The hand prosthesis may comprise a plurality of digits each moveable relative to a main support of the prosthesis, the digits being provided with respective actuators having respective transducers, the control operating the actuators in dependence upon the signals it receives from the transducers in accordance with a signal issued by the user.

The control may be programmed to effect movement of the hand prosthesis to any selected one of a number of different configurations. The latter may comprise a point configuration, a key grip configuration and a precision grip configuration.

Examples of prosthetic apparatus embodying the different aspects of the present invention will now be described in greater detail with reference to the accompanying drawings, in which.

Figure 1:
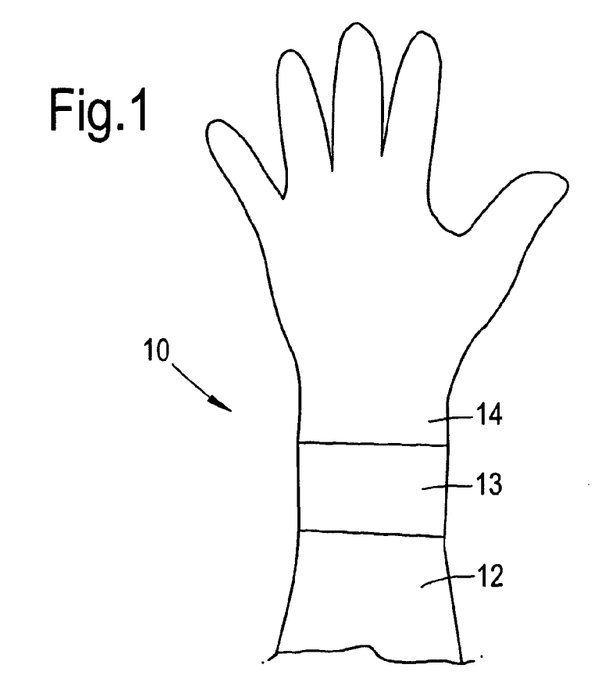
FIG. 1 shows a front view of a prosthesis having an artificial joint embodying the first aspect of the present invention.

The prosthesis 10 shown in FIG. 1 comprises a forearm portion 12, a prosthetic hand portion 14 and a wrist joint interconnecting the forearm portion 12 with the hand portion 14, the joint being covered by a flexible covering 13 which also overlaps a lower part of the hand portion 14 and an upper part of the forearm portion 12.

Figure 2:
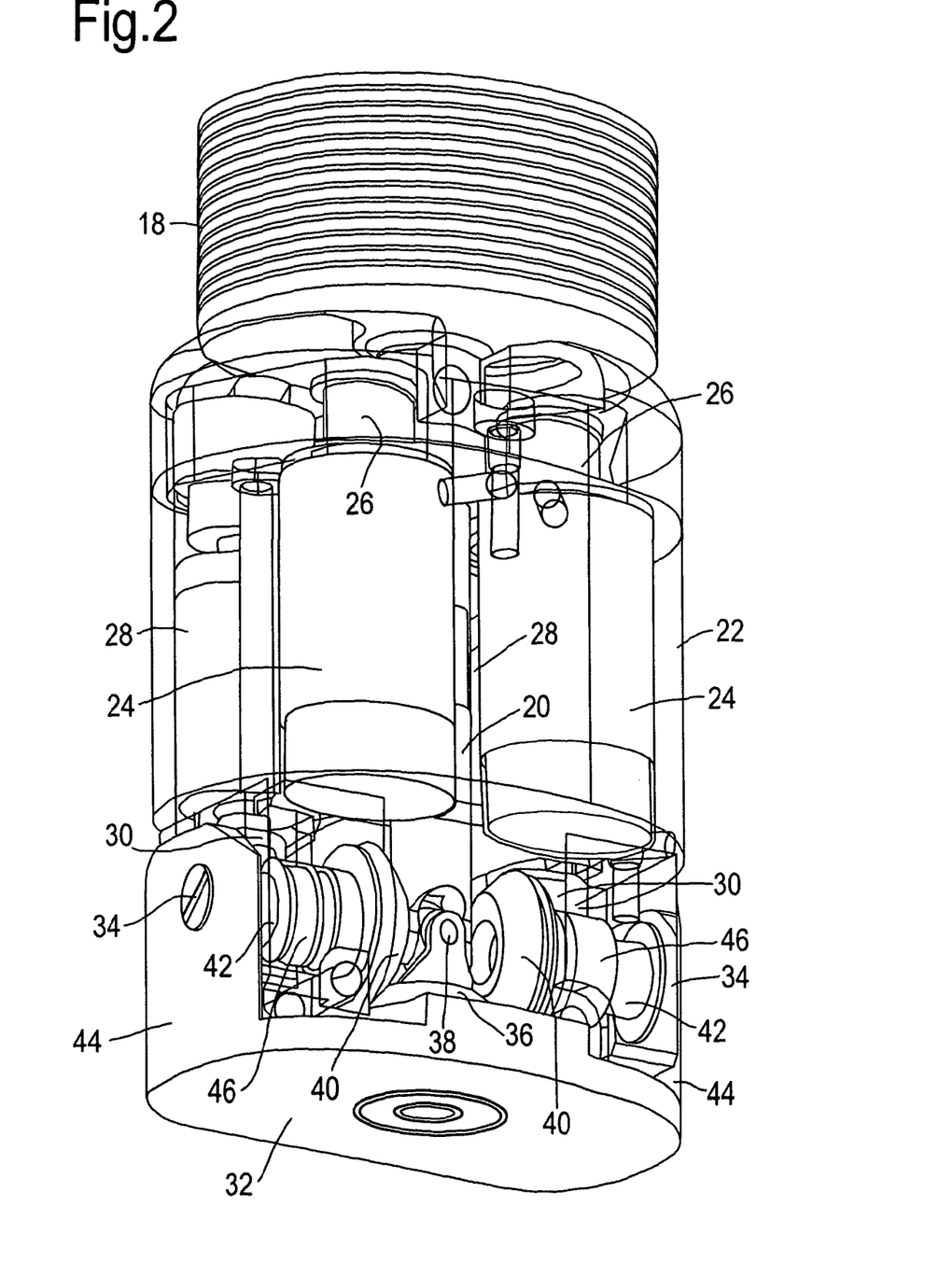
FIG. 2 shows a perspective side partially see-through view of the joint of FIG. 1, inverted relative to the orientation it has in FIG. 1.

The wrist joint mechanism is shown in greater detail in FIG. 2. It comprises a cylindrical attachment part 18, the cylindrical surface of which is grooved to facilitate bonding to the distal end of the forearm portion 12. From the face of the part 18 which is intended to be directed away from the forearm portion 12 extends a rod 20. The rod 20 is thus fixed relative to the part 18. A cylindrical drive housing 22 houses two electrical motors 24. The axis of the housing 22 coincides with that of the rod 20 and the axes of the motors 24 are generally parallel to the rod 20. Respective adjacent ends of the motors 24 are provided with respective drive spindles 26 connected by way of belt drives (not shown) to drive respective gear boxes 28. The latter have respective axes of rotation also generally parallel to the rod 20. The ends of the gear boxes 28 which are further from the part 18 are provided with worm drives 30. The axis of rotation of the motors 24 and the gear boxes are angularly spaced apart around the rod 20. The housing 22, motors 24, and gear boxes 28 are all in a fixed position relative to one another, and together are rotatable around the rod 20.

An articulated part 32 is pivotally connected to the housing 22 by way of pivots 34. It is to this articulated part 32 that the hand portion 14 is attached. The articulated part 32 is able to pivot about the common axis of the pivots 34. A bevelled gearwheel 36 is fixed centrally to the floor of the articulated part 32. The side of the gearwheel 36 nearer to the part 18 is fixed to the distal end of the rod 20 by way of a universal coupling 38.

Two further bevelled gearwheels 40 are arranged with their axes of rotation coincident with one another and so as to engage the wheel 36 at diametrically opposite positions thereof. The gearwheels 40 are mounted on respective axles 42 which extend inwardly from respective sides 44 of the articulated part 32, with their axes in alignment with the pivots 34. The gearwheels 40 therefore have axes of rotation which are at right angles to the axis of rotation of the gearwheel 36. The gearwheels 40 are fixed relative to respective worm wheels 46 engaged to be driven respectively by the worm drives 30.

Figure 3:
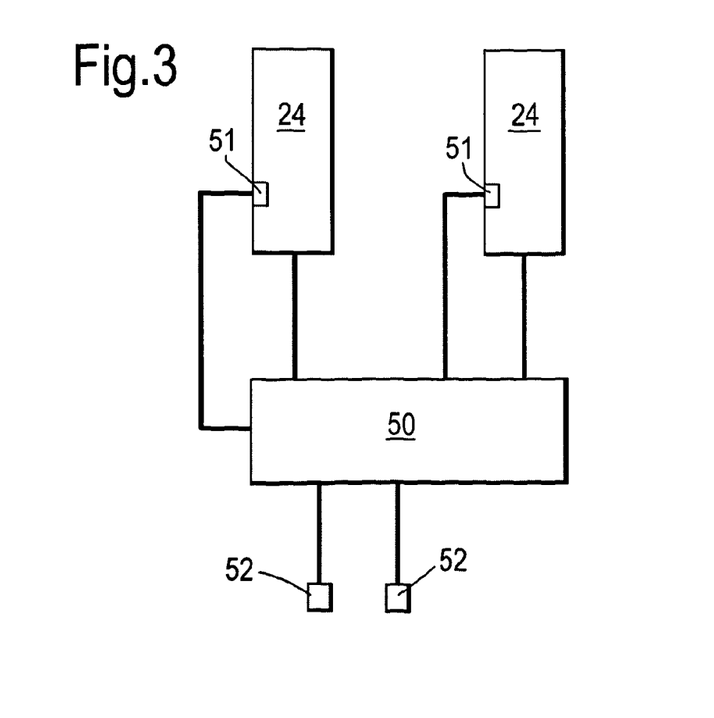
FIG. 3 shows a circuit diagram of simple electrical circuitry of the artificial joint shown in FIGS. 1 and 2.

The electrical circuitry of the prosthetic wrist shown in FIG. 2 is shown in FIG. 3. It comprises a microprocessor 50 connected to each of the motors 24 via respective drive control lines. The motors 24 are equipped with respective sensors 51 indicative of the angular positions of each rotor of the motor 40. The sensors 51 are also connected to the microprocessor 50 to enable closed loop feedback control of the motors 24 by the microprocessor 50. Respective user inputs 52 are also connected to the microprocessor 50 to enable the user to effect a flexing or rotation of the wrist prosthesis respectively, or a combination of flexing and rotation. Such inputs may be connected to motor nerves of the user.

Figure 4:
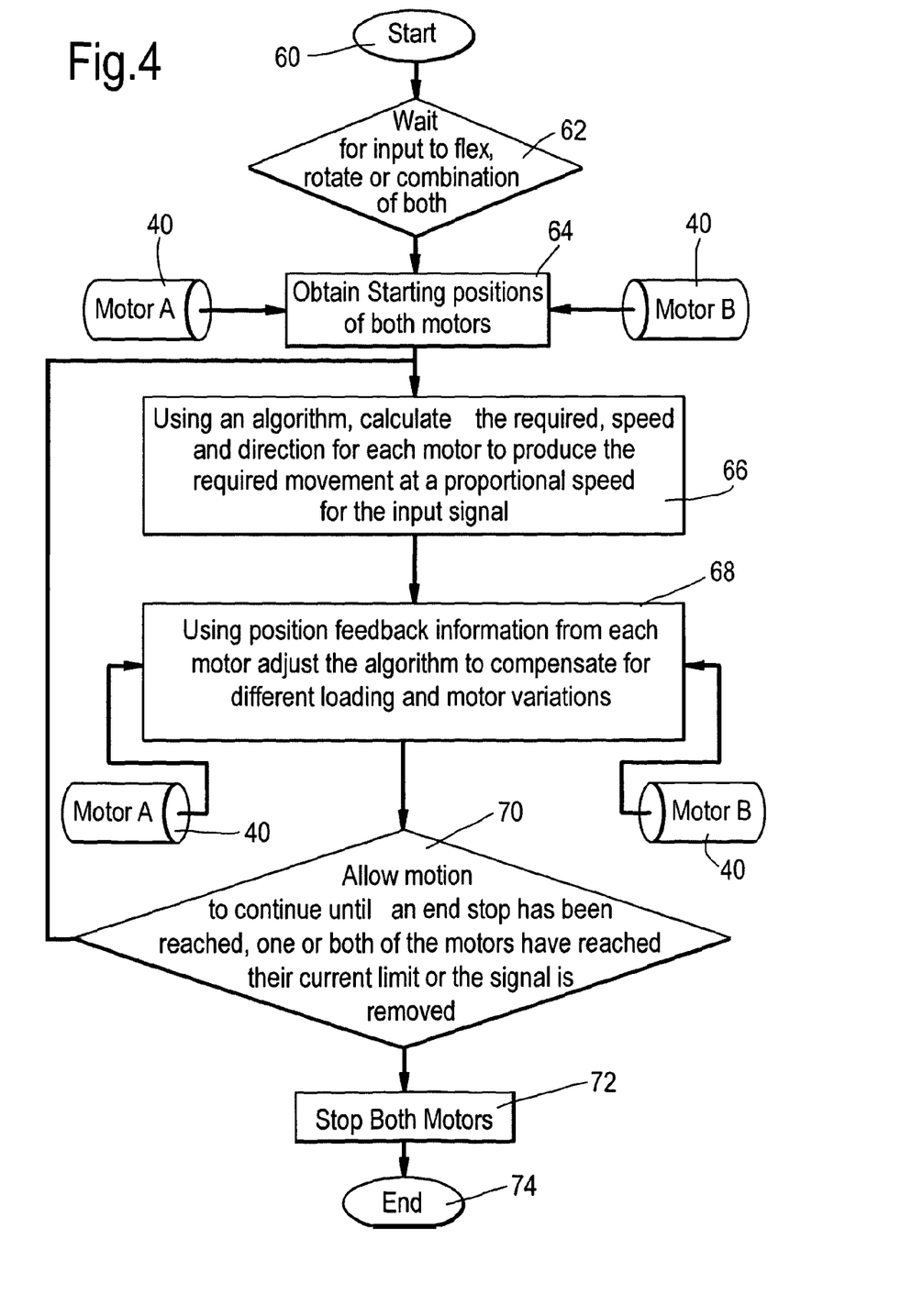
FIG. 4 shows a flow chart of a programme in accordance with which the artificial joint is operated.

Operation of the prosthesis 10 shown in FIGS. 1 to 3 is illustrated by the flow chart shown in FIG. 4.

Thus, from the start position 60 at the top of the flow chart shown in FIG. 4, the microprocessor 50 is programmed to await, at step 62 in the flow chart shown in FIG. 4, an input signal from the user to rotate the two portions 12 and 14 connected at the prosthetic wrist relative to one another or to flex those two parts or to execute a combination of both of these degrees of freedom of movement. This is effected by input signals to the microprocessor 50 via the user inputs 52.

At step 64 in the flow chart shown in FIG. 3, the microprocessor 50 obtains readings from the respective sensors 51 to determine the starting positions of the motors 24. Depending upon the input to the microprocessor 50 from the user inputs 52, the programme executed by the microprocessor 50 determines the speed and direction for each motor to effect the movement required by the user at step 66.

For example, if an input signal to the microprocessor 50 requires a rotation only of the hand portion 14 relative to the arm portion 12 about the longitudinal axis thereof, the motors 24 rotate their respective gearwheels 40 in opposite senses about their common axis of rotation. This will cause the wheels 40 to track around the wheel 36, causing both the articulated part 32 and with it the housing and its contents 22 to rotate about the axis of the rod 20. As a result the lower forearm portion 12 and the hand 14 rotate relative to one another.

If, on the other hand, an input signal to the microprocessor 50 by the input 52 is a command to flex the wrist joint mechanism, the gearwheels 40 are rotated in the same sense. This will cause the gearwheel 36 to move around the common axis of the pivots 30 and consequently the articulated part 32 to be pivoted about the pivots 30, such a flexing being accommodated by the universal coupling 38. This is so regardless of the relative angular position of the articulated part 32 relative to the attachment part 18 about the axis of the rod 20. As a result the lower forearm portion 12 and the hand 14 flex relative to one another.

A combination of these two movements may be effected by the user creating mixed input signals to the microprocessor 50 via the input signals 52. The relative amounts of these two movements are in proportion to these signals.

At step 68 in the flow chart shown in FIG. 4, the programme executed by the microprocessor 50 checks the position of the motors 50 via the inputs the microprocessor receives from the sensors 51. Any discrepancy between the values thus obtained and the desired position according to the input signals to the microprocessor 50 causes the microprocessor 50 to make a corresponding adjustment to the speed and/or sense of rotation of one or both motors 24.

This process continues until step 70 of the programme as shown in FIG. 4, at which stage the input signals to the microprocessor 50 have been removed or an end stop of movement of the wrist joint mechanism has been reached or one or both motors have reached their current limit indicative of a jamming or end stop of the wrist joint mechanism. Both motors 24 are then shut down at step 72 and this routine in the programme by which operation of the microprocessor 50 is determined reaches its end 74.

Numerous variations and modifications to the illustrated prosthesis may occur to the reader without taking it outside the scope of the present invention. Thus, for example, the joint shown in FIG. 1 may be adapted to operate as an elbow joint so that the portions 12 and 14 are respectively ends of upper and lower arm portions.

The bevelled gearwheel 36 may be of larger diameter, and the slant of its bevelling reversed to be inward instead of outward relative to that wheel, and the axles 42 could be mounted on blocks immediately adjacent to and on opposite sides of the universal coupling 38 so that those axles 42 extend outwardly from those blocks as with the gearwheels 40 so that they engage the larger diameter gearwheel 36 at positions thereof diametrically opposite one another. The gearing ratios of the gear boxes 28 and/or the diameter of the gearwheels 40 may correspondingly be altered to take into account the larger diameter of the gearwheel 36.

Furthermore, it will be appreciated that although what is shown in FIGS. 1 to 4 comprises a wrist prosthesis, it may equally be an artificial wrist for a robot.

Figure 5:
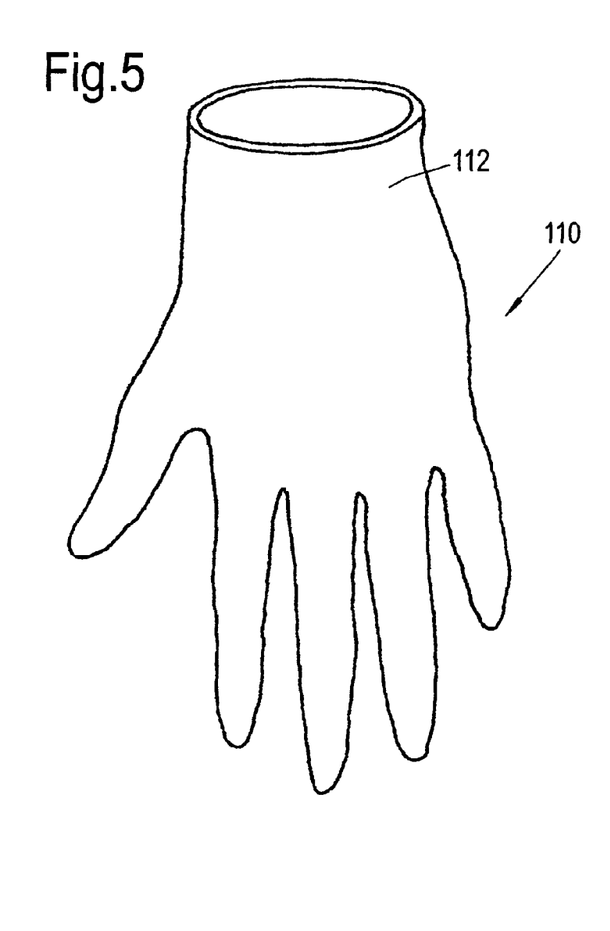
FIG. 5 shows a perspective rear view of a mould for a cover for a prosthesis hand.

The mould 110 shown in FIG. 5 is hollow and has the shape of a glove so that its interior has the shape of a hand. It is open at a position corresponding to the wrist 112. The mould 110 is pre-warmed and pretreated on its interior surface with a release agent. A liquid silicone rubber mixed with solvent is poured into the mould 110, and the mould 110 is plugged at the wrist 112. The silicone is one which gives good wear resistance and a relatively high tear strength whilst at the same time providing good elasticity. The mould is inserted into a motion machine which will not be described in detail as readers familiar with the art will be fully aware of the construction of such a machine. The machine moves the mould 110 to evenly distribute the liquid silicone rubber over the interior of the mould. The amount of liquid poured into the mould 110 is such as to provide a layer of thickness of the silicone rubber of about 0.12 mm.

Such moulding is known as rotational or slush moulding.

The mould is then removed from the motion machine, unplugged and orientated so that excess silicone is allowed to drain away.

One or more further layers of the silicone mixed with solvent are deposited in the interior of the mould 110 in this way by repeating this procedure.

A number of layers of a second silicone mixed with solvent are then built up on the interior of the mould 110, onto the layers of the first silicone, so that there are in all a total of twelve layers of silicone built up on the interior of the mould 110. The second silicone is one which gives the finished article a softness and a high degree of flexibility and also renders the cover lifelike and close in appearance and behaviour to human skin. It will be appreciated that the number of layers may be fewer or greater than twelve.

The mould with these layers is then placed into an oven to cure the silicone.

The mould is then removed from the oven, allowed to cool and the cover pre-form 114 is then extracted from the mould interior.

Figure 6:
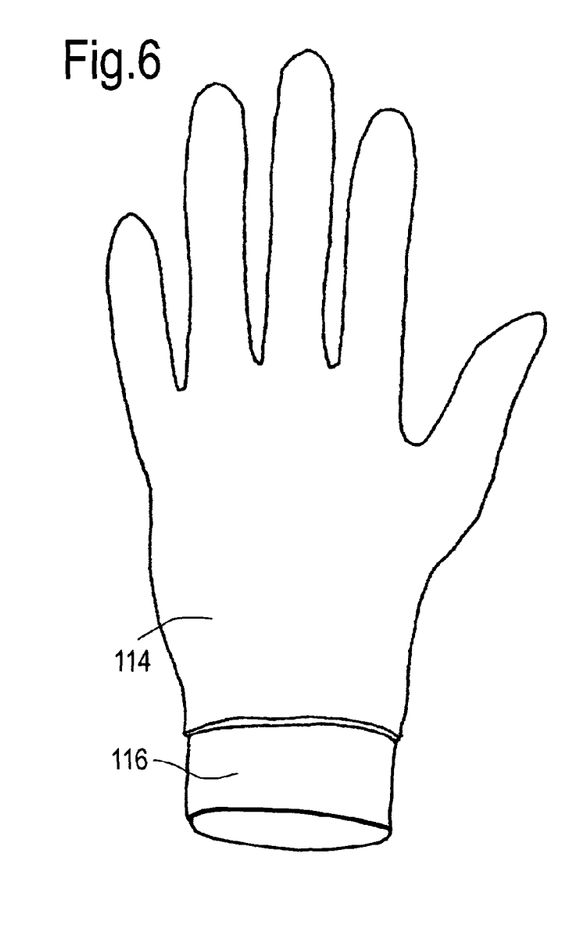
FIG. 6 shows a perspective front view of a mandrel bearing a cover made from the mandrel shown in FIG. 5.

The cover pre-form 114 is then turned inside out and then placed on an appropriately shaped mandrel or former 116, as shown in FIG. 6. A pre-formed reinforcing glove shaped woven nylon matrix or mesh is then placed over the cover pre-form 114. The strand diameter of the nylon mesh is substantially 0.3 mm. A blend of liquid silicone, rubber and solvent is now applied by roller or brush to the cover pre-form 114. This technique impregnates the matrix or mesh, encapsulates it, and glues it to the silicone laminate. A second application of such a blend may be applied to the matrix or mesh so as to uniformly coat the cover pre-form. The mandrel with cover is now placed in an oven to cure the further applied silicone.

Figures 7, 7A, 8:
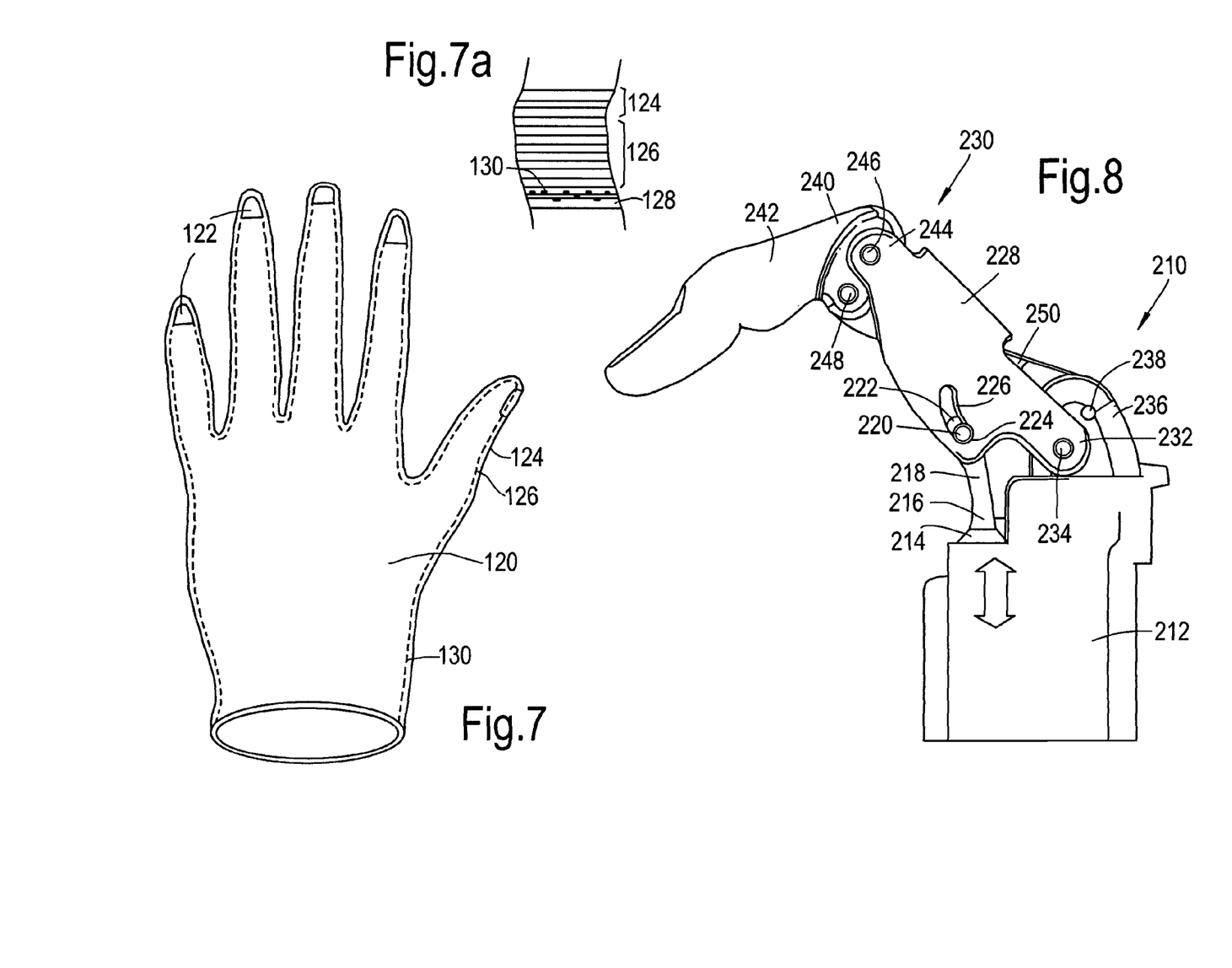
FIG. 7 shows a perspective rear view of a cover made in accordance with the second aspect of the present invention with the mould and the mandrel shown in FIGS. 5 and 6.
FIG. 7a shows a cross-sectional diagram on a very much larger scale of the material of the cover shown in FIG. 7.
FIG. 8 shows a side view of a device embodying the third aspect of the present invention with the parts thereof having first relative positions.

After curing the mandrel with cover is removed from the oven and allowed to cool to room temperature, whereupon the finished cover 114 is peeled off from the mandrel 116. The finished cover 120 for a prosthetic hand is shown in FIG. 7. It will be seen that prosthetic fingernails 122 have been attached by depositing and curing further layers of silicone on to the cover 120 at the fingertips thereof, comprising at least one layer of pink silicone covered by at least one layer of clear silicone, to a thickness of substantially 2.5 mm.

A section through a portion of the cover 120 is now as shown in FIG. 7a. The outermost layers 124 of silicone comprise the first silicone and the middle layers 126 of silicone comprise the second silicone. Within the innermost layer of silicone 128 there is embedded the nylon mesh 130.

Numerous variations and modifications to the illustrated method of manufacturing the prosthetic cover, as well as the prosthetic cover itself may occur to the skilled reader without taking the resulting construction outside the scope of the present invention. For example, there may be fewer layers of silicone, or more layers of silicone, in the finished cover 120.

Figure 9:
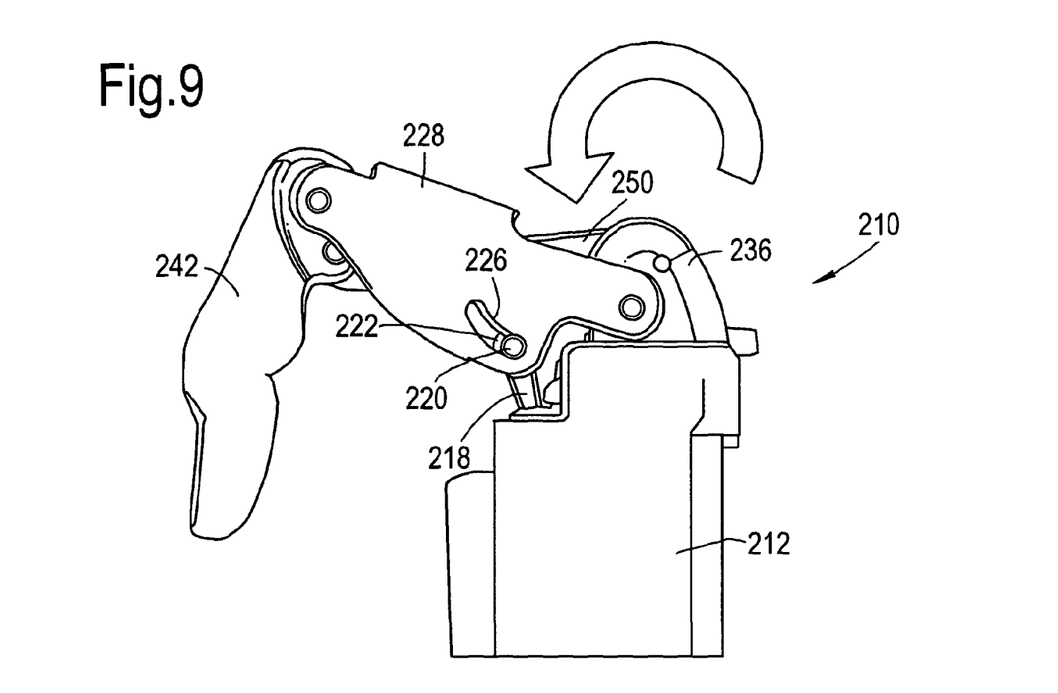
FIG. 9 shows a further side view of the device shown in FIG. 8, but with the parts thereof having second relative positions.
Figure 10:
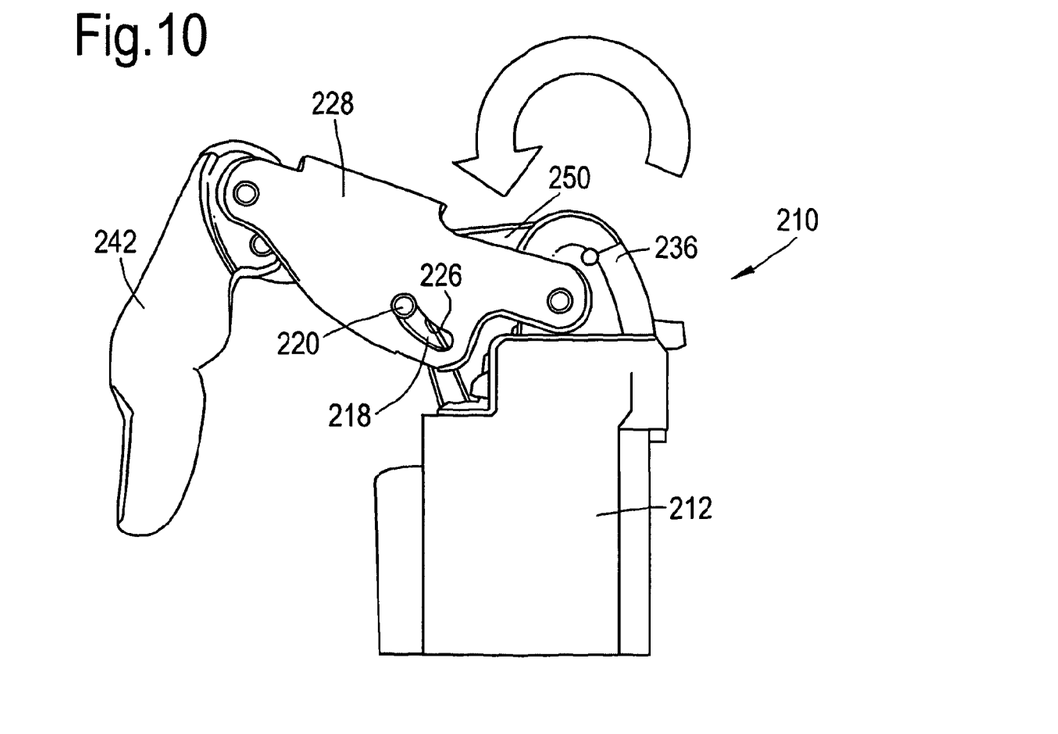
FIG. 10 shows a side view of the prosthetic device shown in FIGS. 8 and 9 with the parts thereof having yet further different relative positions.

The prosthetic device 210 shown in FIGS. 8 to 10 is constituted by a myoelectric prosthetic hand device and comprises a base part 212 constituting a palm of the prosthetic device in which is housed a linear actuator drive motor 214. A lower end 216 of a tendon 218 is secured to this linear actuator drive motor 214. A spigot 220 is provided on and fixed to the opposite end 222 of the tendon 218 and engages a lower end 224 of a slightly arcuate slot 226 formed in the lower half of a first or proximal phalange 228 of a finger 230 of the prosthetic device 210.

A lower end 232 of the first phalange 228 is pivoted at a pivot 234 to a mount 236 which constitutes a knuckle of the prosthesis and which is fixed to the base 212 rearwardly and above the linear actuator drive motor 214.

The slightly arcuate slot 226 has its concave side closer to the mount 236.

A further pivot 238, provided on the mount 236, is set rearwardly and above the pivot 234.

A rearward end 240 of a second phalange 242 is pivoted to an upper end 244 of the first phalange 228 by way of a pivot 246. The rearward end 240 of the phalange 242 is provided with a second pivot 248 positioned, in the setting shown in FIG. 8 in which the finger 230 is in an open position, below and forwardly of the pivot 246. A ligament 250 extends between and is pivoted to the mount 236 and the second phalange 242 at the pivots 238 and 248 respectively by respective through-pins.

When the linear actuator drive motor 214 is operated, it retracts the tendon 218 into the base or palm 212 so that the spigot 220 is lowered when the prosthetic device is orientated as shown in FIG. 8. This causes the first phalange 228 to pivot in an anti-clockwise sense, viewing it as in FIG. 8, about the pivot 234. At the same time, because the spacing between the pivots 238 and 248 is fixed by the ligament 250, the second phalange 242 pivots about the pivot 246 towards the first phalange 228. This results in the closure of the finger 230 towards the base or palm 212, so that the parts of the prosthetic device have the relative positioning shown in FIG. 9.

Release of the retracting force on the tendon 218 enables the finger 213 to be restored to the position it has in FIG. 8. This may be effected by means of an elastic covering or glove (not shown) or by means of internal springs (not shown) of the prosthetic device.

In the event that an external force should be applied to for example the said second phalange 242, causing inward deflection thereof so as to urge it towards the base or palm 212, without operation of the linear actuator drive motor 214, the likelihood of damage is reduced by virtue of the slot 228 enabling the spigot 220 to ride up away from the end 224 of the slot 226 towards the opposite end thereof, so that the tendon 218 and the motor 214 and/or other parts of the prosthetic device, are not damaged, the parts of the prosthetic device then adopting the relative positioning shown in FIG. 10, or any positioning intermediate between that shown in FIG. 8 and that shown in FIG. 9.

Numerous modifications and variations to the illustrated prosthetic device may occur to the reader without taking the resulting construction outside the scope of the present invention. For example, there may be a plurality of fingers 230 with respective tendons 218 and motors 214 arranged side by side on the base or palm 212, imitating the four fingers of a hand. A similarly constructed thumb may also be provided on the prosthetic device.

At the same time, it will be appreciated that the present invention is not limited to prosthetic devices which imitate a hand, so that the protective slot construction, which may be considered to be an over-travel feature, may be embodied in a foot prosthetic device or in for example an arm prosthetic device or a leg prosthetic device.

Figure 11:
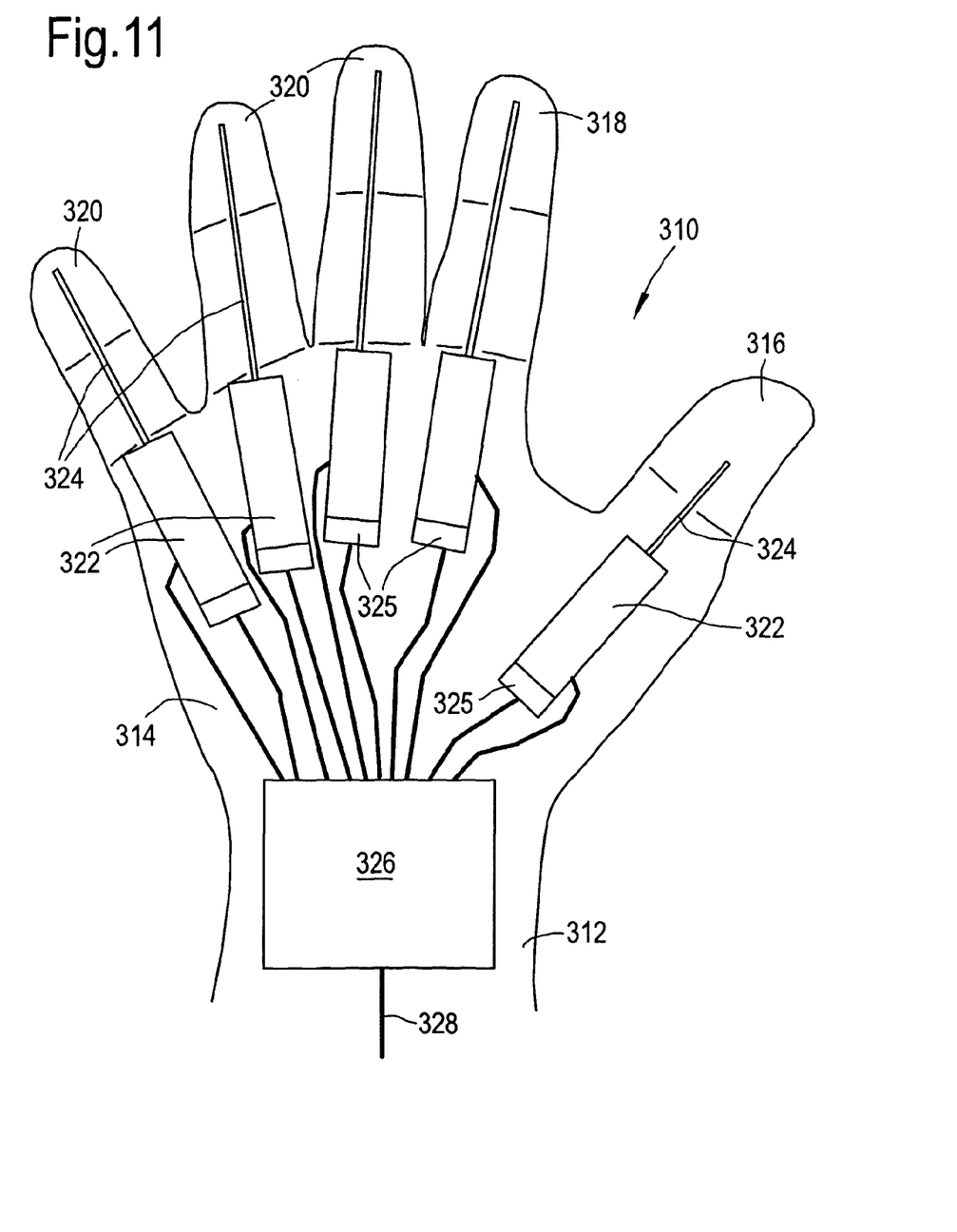
FIG. 11 shows a diagram of a hand prosthesis embodying the fourth aspect of the present invention from its front, including electrical circuitry thereof.

FIG. 11 shows a hand prosthesis 310 comprises a wrist portion 312 from which extends a main support or palm portion 314. From this extends a thumb digit 316, and index finger digit 318, and three further finger digits 320, each being jointed so that it can be curled up or straightened up as with an actual hand. Respective actuators 322 are provided for the digits, the actuators having respective ligaments 324 to enable them to effect such curling up and/or straightening.

Each actuator 322 is also provided with a movement transducer in the form of a digital pulse encoder 325. Each actuator 322 is connected to a control processor 326 to be controlled thereby, and each transducer 325 is connected to the control to deliver signals thereto indicative of the movement effected by its associated actuator 322, both in amount and direction. An input 328 to the processor 326 enables the user to initiate movement of the digits, for example by movement of a selected muscle of the user.

Figure 12:
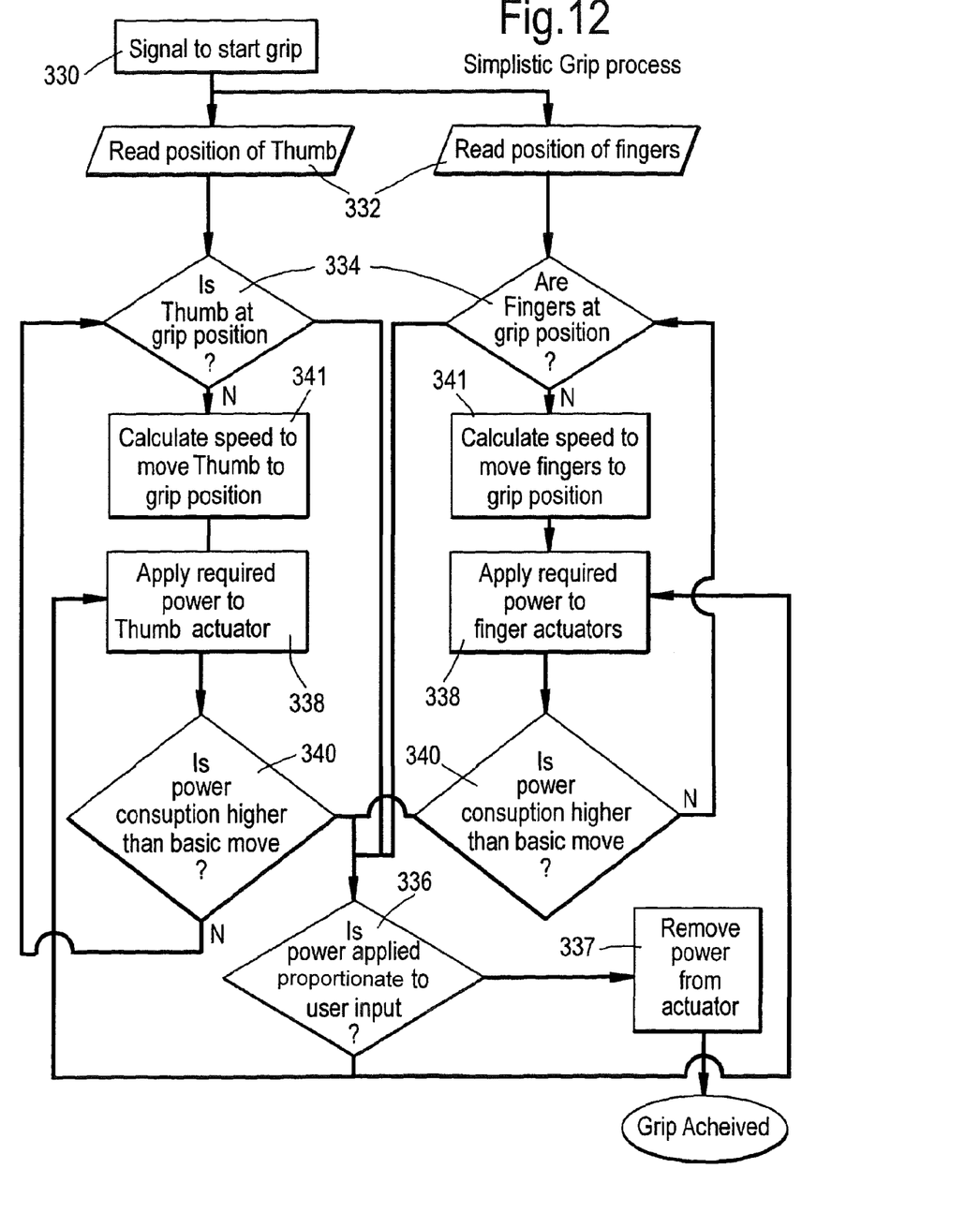
FIG. 12 shows a flow chart of a software program by which a control of the prosthesis shown in FIG. 11 is programmed to operate.

The manner in which signals issued by the transducers 325 are used by the processor 326 to effect movement of the digits of the prosthesis 310 is shown by the flow chart of FIG. 12.

Thus the program is commenced by a command signal at the input 328 recognised by the control processor 326, indicated by step 330 in FIG. 12. The current actual positions of the digits held in memory locations within the processor 326, as constantly updated by the transducers 325, are read by the control at steps 332. If both the thumb and the finger digits are already in the correct positions for the selected movement, as determined at steps 334, the program moves to step 336 at which a check is made whether the power applied is proportional to that selected by the user at step 330. If it is, the control removes the application of power to the actuators 322 at step 337 since this is indicative of the required grip having been achieved. Otherwise the program is advanced to steps 338 in which the required power is applied to the digit actuators. There follows the interrogation at step 340 as to whether power consumption is greater than that required for movement of the digit. If it is that is indicative that the grip has been closed and the program is forwarded to step 336. Otherwise it is returned to the steps 334. If the digits are nonetheless in the correct position, the program is advanced to step 336. If not, the control processor calculates the required speed to move the digit or digits at steps 341 by comparing the actual position of each digit with the desired position stored in the control processor 326.

These steps result in constant movement rates for the digits.

Figure 13:
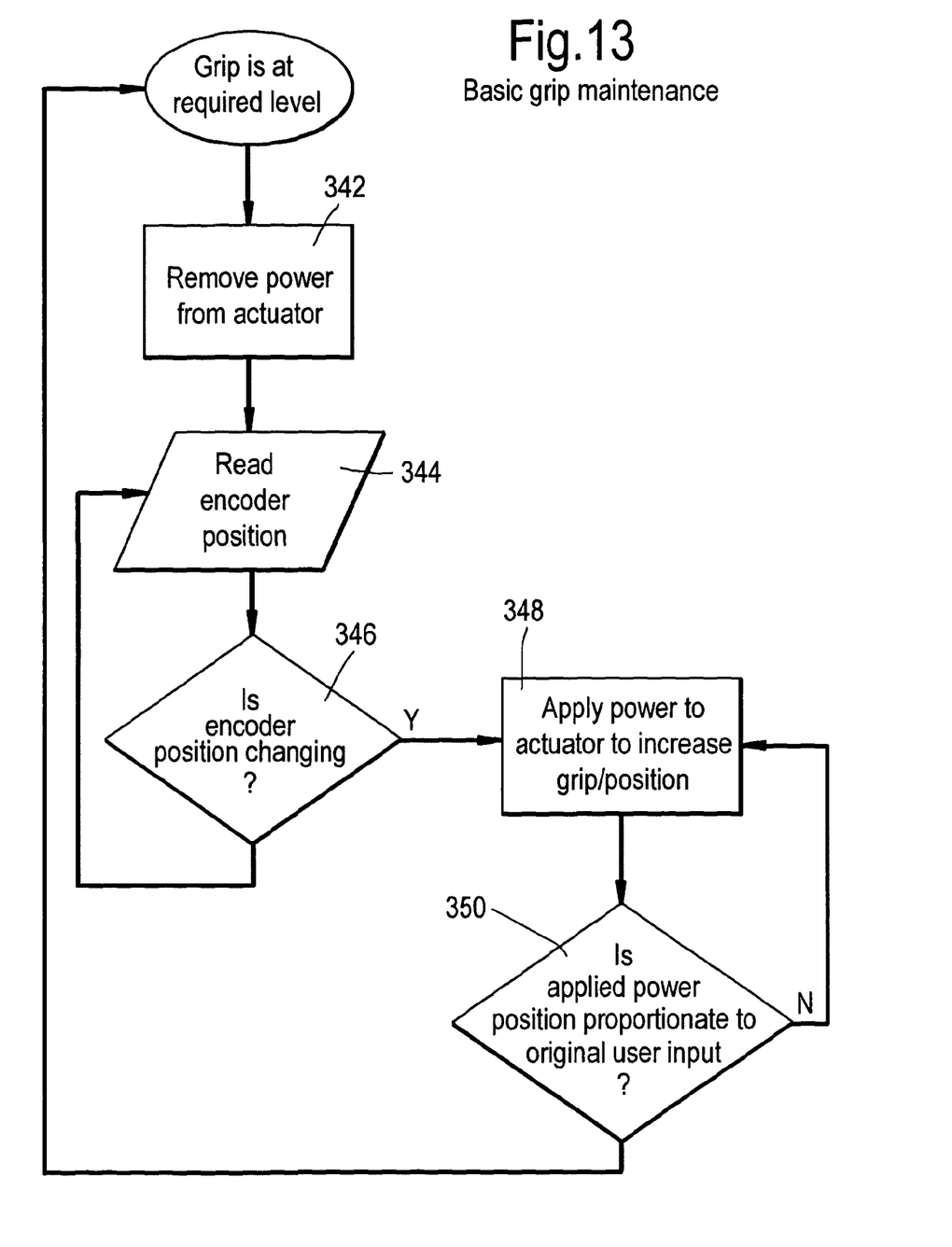
FIG. 13 shows a flow chart of a further software program by which a control of the prosthesis shown in FIG. 11 is programmed to operate.

FIG. 13 shows how the grip is maintained at the desired level. Once the desired grip is achieved, the grip maintenance program shown in this FIGURE is initiated. With the grip at the required level power is removed from the or each actuator at step 342. At step 344 the digit position is read. The query as to whether that position is changing is raised at step 346. If it is, power is applied to increase the grip or move the digit to the required grip position at step 348. If the applied power is proportional to the original input signal determined at step 350, the program returns to step 342. Otherwise it returns to step 348. A slip sensing function is thereby achieved.

Figure 14:
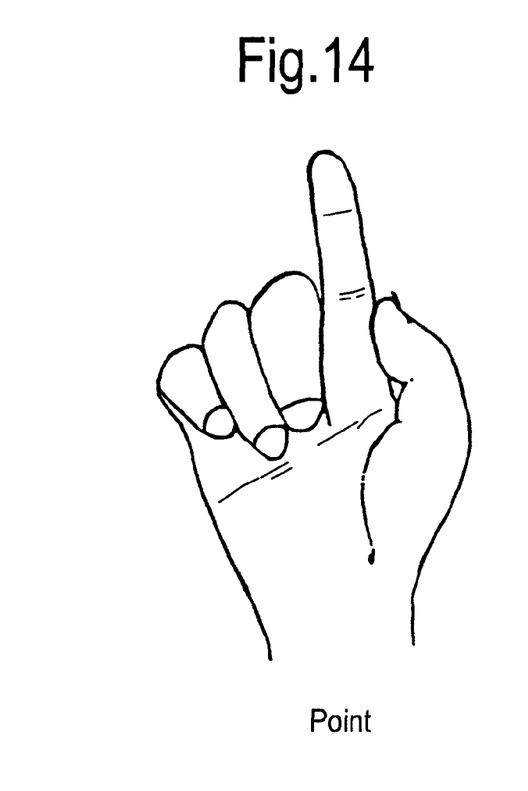
FIGS. 14 to 16 show respective front views of the prosthesis shown in FIG. 11 after it has been moved into different respective selectable configurations.
Figure 15:
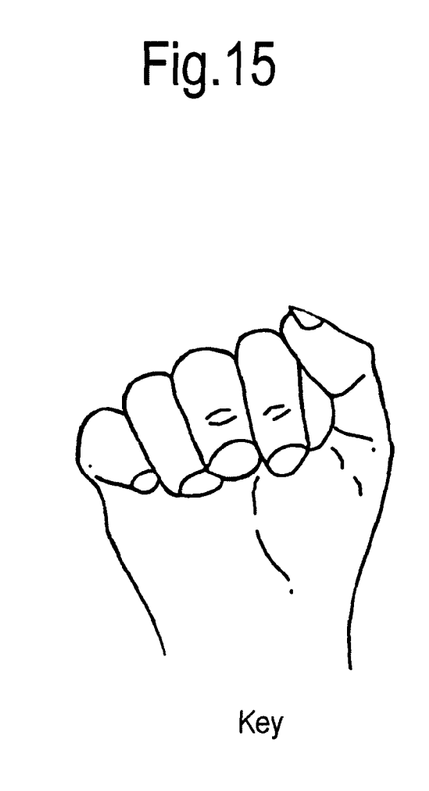
Figure 16:
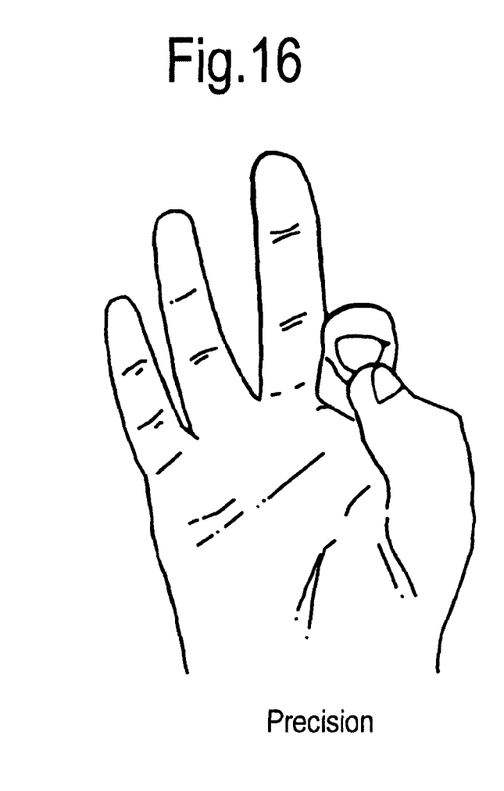

Any selected one of a number of different programs stored in the control processor may be effected by a corresponding signal applied by the user to the input 328, to effect movement of the prosthesis into respective different configurations shown in FIGS. 14, 15 and 16, being point, key grip and precision grip configurations respectively.

Numerous variations and modifications to the illustrated prosthesis may occur to the reader without taking it outside the scope of the present invention. To give one example only, the three further finger digits may be controlled by one and the same actuator.

The invention claimed is:

1. A hand prosthesis (310) comprising a plurality of digits (316, 318, 320) each movable relative to a main support (314) of the prosthesis (310), respective actuators (322) of the digits (316, 318, 320), a control processor (326) connected to operate the actuators (322) in dependence upon signals issued to the control processor (326) by the user, and transducers (325) connected to the control processor (326) and also respectively to the actuators (322) to provide signals to the control processor (326) indicative of the amount of movement effected by the actuators (322), in which the actuators (322) are operated by the control processor (326) in dependence upon the signals it receives from the transducers (325) and in accordance with the signals issued by the user, characterized in that the current actual positions of the digits (316, 318, 320) are held in memory locations within the control processor (326) and are constantly updated by the transducers (325) when the hand prosthesis (310) is in use, and in that the desired positions of the digits (316, 318, 320) are stored in memory locations within the control processor (326), and the latter is programmed to calculate the required speeds to move the digits (316, 318, 320) by comparing the actual positions with the desired positions of each digit (316, 318, 320).

2. A hand prosthesis (310) according to claim 1, in which each movement transducer (325) comprises a digital pulse encoder.

3. A hand prosthesis according to claim 1, in which each actuator comprises an electrical motor.

4. A hand prosthesis according to claim 1, in which the control processor (326) is programmed to effect movement of the hand prosthesis (310) to any selected one of a number of different configurations.

5. A hand prosthesis according to claim 1, in which the different configurations comprise a point configuration, a key grip configuration and a precision grip configuration.

* * * * *